(12) United States Patent
Matsumoto et al.

(10) Patent No.: US 9,993,415 B2
(45) Date of Patent: Jun. 12, 2018

(54) HAIR TREATMENT AGENT AND METHOD FOR CAUSING MODIFIED PEPTIDE TO PENETRATE INTO HAIR

(71) Applicant: MILBON CO., LTD., Osaka-shi, Osaka (JP)

(72) Inventors: Yohei Matsumoto, Osaka (JP); Atsushi Yamada, Osaka (JP); Naoto Matsumoto, Moriguchi (JP)

(73) Assignee: MILBON CO., LTD., Osaka-Shi, Osaka (JP)

( * ) Notice: Subject to any disclaimer, the term of this patent is extended or adjusted under 35 U.S.C. 154(b) by 0 days. days.

(21) Appl. No.: 15/248,480

(22) Filed: Aug. 26, 2016

(65) Prior Publication Data

US 2017/0071843 A1 Mar. 16, 2017

(30) Foreign Application Priority Data

Sep. 15, 2015 (JP) .................. 2015-181416

(51) Int. Cl.
*A61K 8/64* (2006.01)
*A61Q 5/00* (2006.01)

(52) U.S. Cl.
CPC ................ *A61K 8/64* (2013.01); *A61Q 5/002* (2013.01)

(58) Field of Classification Search
CPC .................................. A61Q 5/002; A61K 8/64
USPC .................................................. 1/1
See application file for complete search history.

(56) References Cited

U.S. PATENT DOCUMENTS

2004/0047825 A1* 3/2004 Denzer ..................... A61K 8/39
424/70.12

FOREIGN PATENT DOCUMENTS

| EP | 0002506 A1 | 6/1979 |
|---|---|---|
| JP | S5831324 B2 | 7/1983 |
| JP | S62221615 A | 9/1987 |
| JP | H10251127 A | 9/1998 |
| JP | 2011144127 A | 7/2011 |
| JP | 2012056855 A | 3/2012 |
| JP | 2012224573 A | 11/2012 |
| JP | 2013014557 A | 1/2013 |

OTHER PUBLICATIONS

Jc.; title: Are the sulfate free shampoos really gentler? The natural haven online blogs; published Jun. 8, 2012.*
Schill&Seilacher; title: amino acid based surfactants; published Oct. 10, 2010. downloaded from http://rossorg.com/images/stories/Product_PDFs/Schill_Seilacher/General_Brochure_Oct_2010. pdf.*
Decision of Refusal in JP Application No. 2015-181416, dated Mar. 21, 2017.

* cited by examiner

*Primary Examiner* — Yanzhi Zhang
(74) *Attorney, Agent, or Firm* — Hauptman Ham, LLP

(57) ABSTRACT

A hair treatment agent in which penetrability of a modified peptide into the internal structure of the hair can be enhanced even under the conditions of acidic pH, and a method for causing a modified peptide to penetrate into the hair, are provided.

Disclosed is a hair treatment agent at a pH of from 3.5 to 5.5, the hair treatment agent including: (A) a modified peptide having one kind or two or more kinds of side chain groups selected from a side chain having a structure represented by the following Formula (I), a side chain group having a salt of a structure represented by the following Formula (I), a side chain group having a structure represented by the following Formula (II), a side chain group having a salt of a structure represented by the following Formula (II), a side chain group having a structure represented by the following Formula (III), and a side chain group having a salt of a structure represented by the following Formula (III); and (B) an anionic surfactant:

$$-S-S-(CH_2)_n-COOH \quad (I)$$

(wherein in Formula (I), n represents 1 or 2)

$$-S-S-CH(CH_3)-COOH \quad (II)$$

$$-S-S-CH(COOH)-CH_2-COOH \quad (III).$$

7 Claims, 8 Drawing Sheets
(8 of 8 Drawing Sheet(s) Filed in Color)

FIG. 2
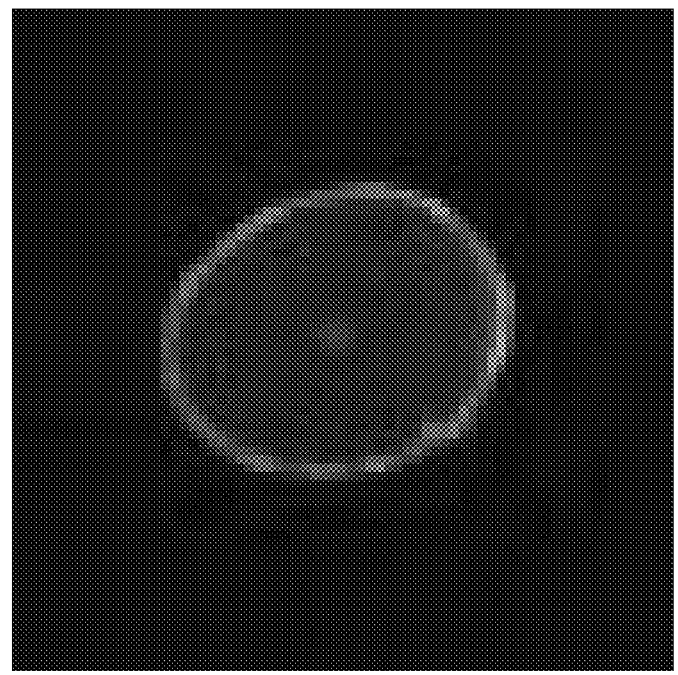
Comparative Example 3a
(Cationic Surfactant)
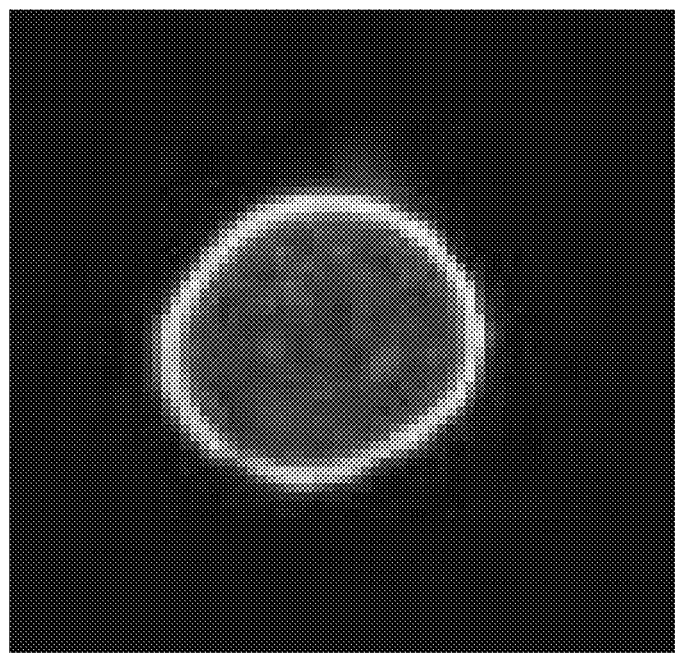
Example 3a
(Anionic Surfactant)

HAIR TREATMENT AGENT AND METHOD FOR CAUSING MODIFIED PEPTIDE TO PENETRATE INTO HAIR

The present application claims priority benefit of Japanese Patent Application No. JP2015-181416, filed Sep. 15, 2015, and this application, including the specification, claims, drawings, and abstract, is incorporated herein by reference in its entirety for all purposes.

TECHNICAL FIELD

Embodiments of the invention relate to a hair treatment agent having a predetermined modified peptide incorporated therein, and a method for causing a modified peptide to penetrate into the hair.

BACKGROUND

Peptides that are obtainable by hydrolyzing proteins are incorporated into compositions used for hair applications, in expectation of a hair restoring effect or a hair conditioning effect. Also, research and development aimed at an enhancement of the effects of such peptides or addition of functions of such peptides has been carried out, and as a result, cationized, acylated, or silylated peptide derivatives are now known.

JP 2011-144127 A discloses, as a peptide derivative to be incorporated into a hair treatment agent, a modified peptide obtainable by introducing a carboxymethyl disulfide group into a peptide using a thioglycolate. It is considered that when this modified peptide is used, a restoring effect in the hair can be expected.

Furthermore, JP 2012-056855 A discloses a modified peptide having a carboxyl group as an introduced group, which is obtainable using a thioglycolate, a thiolactate, or a thiomalate.

SUMMARY

However, in regard to hair that has been damaged, it is desirable to increase the penetrability of a modified peptide into the hair in order to repair the internal structure of the hair.

Embodiments of the invention have been made in view of the demand described above, and an object of the embodiments is to provide a hair treatment agent that is capable of enhancing penetrability of a modified peptide into the internal structure of the hair even under acidic pH conditions, and a method for causing a modified peptide to penetrate into the hair.

The present inventors conducted a thorough investigation, and as a result, they found that in a hair treatment agent having a predetermined modified peptide incorporated therein, even if the pH of the hair treatment agent is from 3.5 to 5.5, when an anionic surfactant is incorporated into the hair treatment agent, penetrability of the modified peptide into the hair is increased. Thus, the inventors completed the embodiments.

That is, a hair treatment agent related to the embodiments of the invention is a hair treatment agent having a pH of from 3.5 to 5.5, the hair treatment agent including (A) a modified peptide having one kind or two or more kinds of side chain groups selected from a side chain group having a structure represented by the following Formula (I), a side chain group having a salt of a structure represented by the following Formula (I), a side chain group having a structure represented by the following Formula (II), a side chain group having a salt of a structure represented by the following Formula (II), a side chain group having a structure represented by the following Formula (III), and a side chain group having a salt of a structure represented by the following Formula (III); and (B) an anionic surfactant:

$$-S-S-(CH_2)_n-COOH \quad (I)$$

(wherein in Formula (I), n represents 1 or 2)

$$-S-S-CH(CH_3)-COOH \quad (II)$$

$$-S-S-CH(COOH)-CH_2-COOH \quad (III).$$

The (B) anionic surfactant of the hair treatment agent includes one kind or two or more kinds selected from, for example, an alkyl ether sulfate, an alkyl ether carboxylate, an α-olefin sulfonate, and an N-acyl amino acid salt.

The pH of the hair treatment agent is, for example, from 4.0 to 5.5.

The hair treatment agent is, for example, a liquid formulation.

The viscosity of the hair treatment agent is, for example, 1,000 mPa·s or less.

A method for causing a modified peptide to penetrate into the hair related to the embodiments includes causing a modified peptide to penetrate into the hair under the conditions of a pH of from 3.5 to 5.5 in the co-presence of an anionic surfactant, the modified peptide being a modified peptide having one kind or two or more kinds of side chain groups selected from a side chain group having a structure represented by the following Formula (I), a side chain group having a salt of a structure represented by the following Formula (I), a side chain group having a structure represented by the following Formula (II), a side chain group having a salt of a structure represented by the following Formula (II), a side chain group having a structure represented by the following Formula (III), and a side chain group having a salt of a structure represented by the following Formula (III):

$$-S-S-(CH_2)_n-COOH \quad (I)$$

(wherein in Formula (I), n represents 1 or 2)

$$-S-S-CH(CH_3)-COOH \quad (II)$$

$$-S-S-CH(COOH)-CH_2-COOH \quad (III).$$

When the hair treatment agent and the method for causing a modified peptide to penetrate into the hair of the embodiments are used, even if the pH is from 3.5 to 5.5, the hair penetrability of the modified peptide can be enhanced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows fluorescence microscopic observation photographs of Example 3a and Comparative Example 3a;

FIG. 5 shows photographs showing the dispersion state of Examples 6a to 6d and Comparative Example 6a;

FIG. 7 shows photographs showing the dispersion state of Examples 8a to 8k and Comparative Example 8a; and FIG. 8 shows photographs showing the dispersion state of Examples 9a to 9j and Comparative Example 9a.

DETAILED DESCRIPTION

Figure 1:
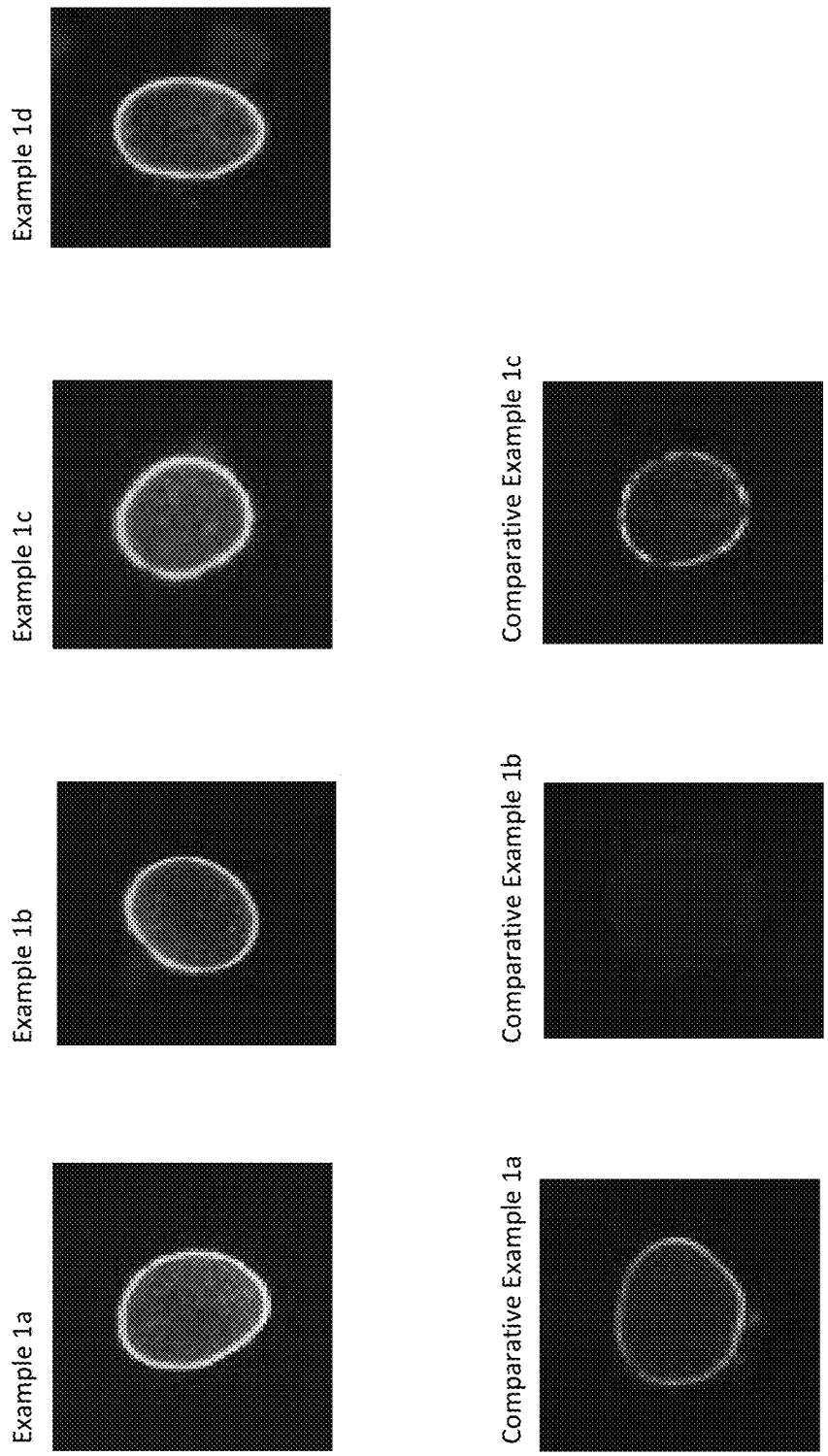
FIG. 1 shows fluorescence microscopic observation photographs of Examples 1a to 1d and Comparative Examples 1a to 1c.
Figure 3:
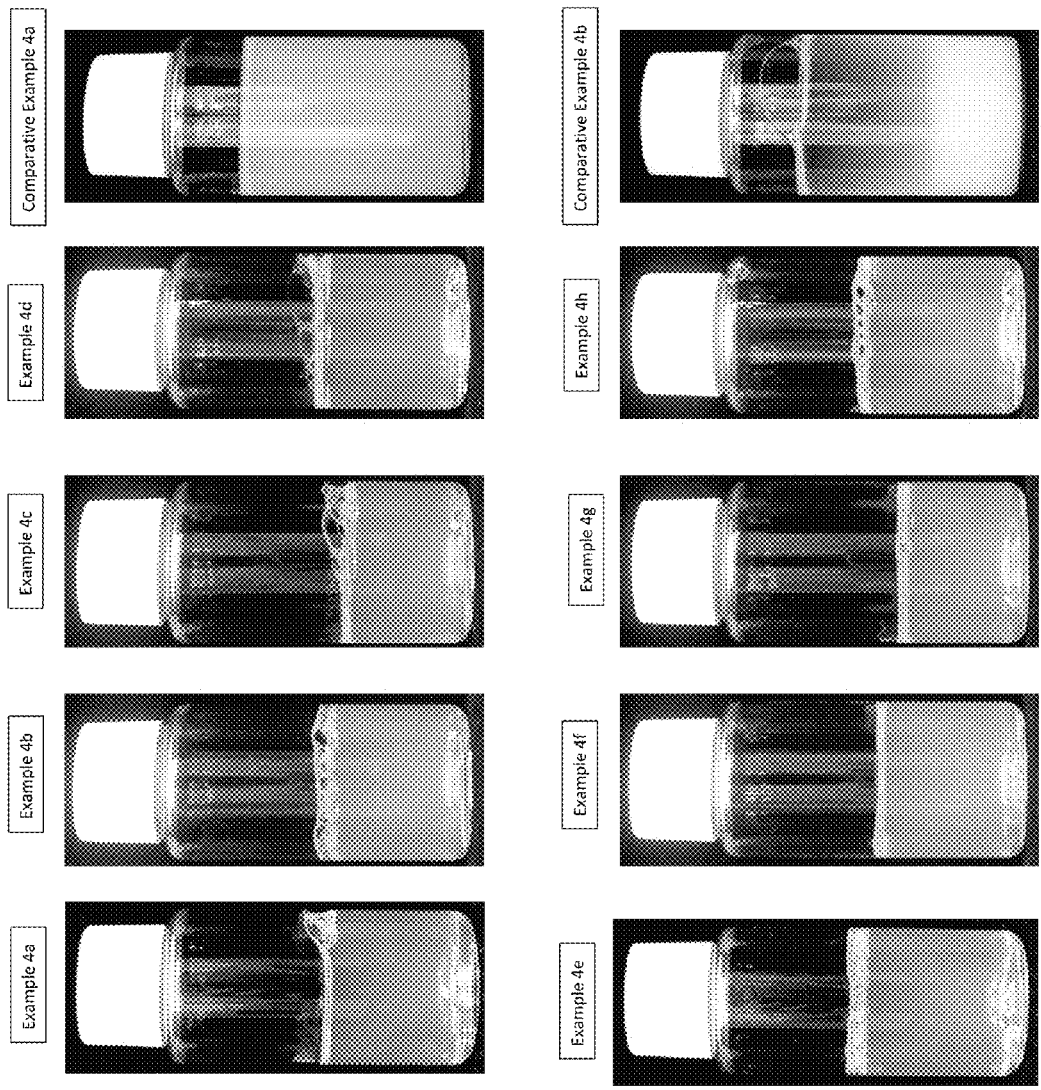
FIG. 3 shows photographs showing the dispersion state of Examples 4a to 4h and Comparative Examples 4a and 4b.
Figure 4:
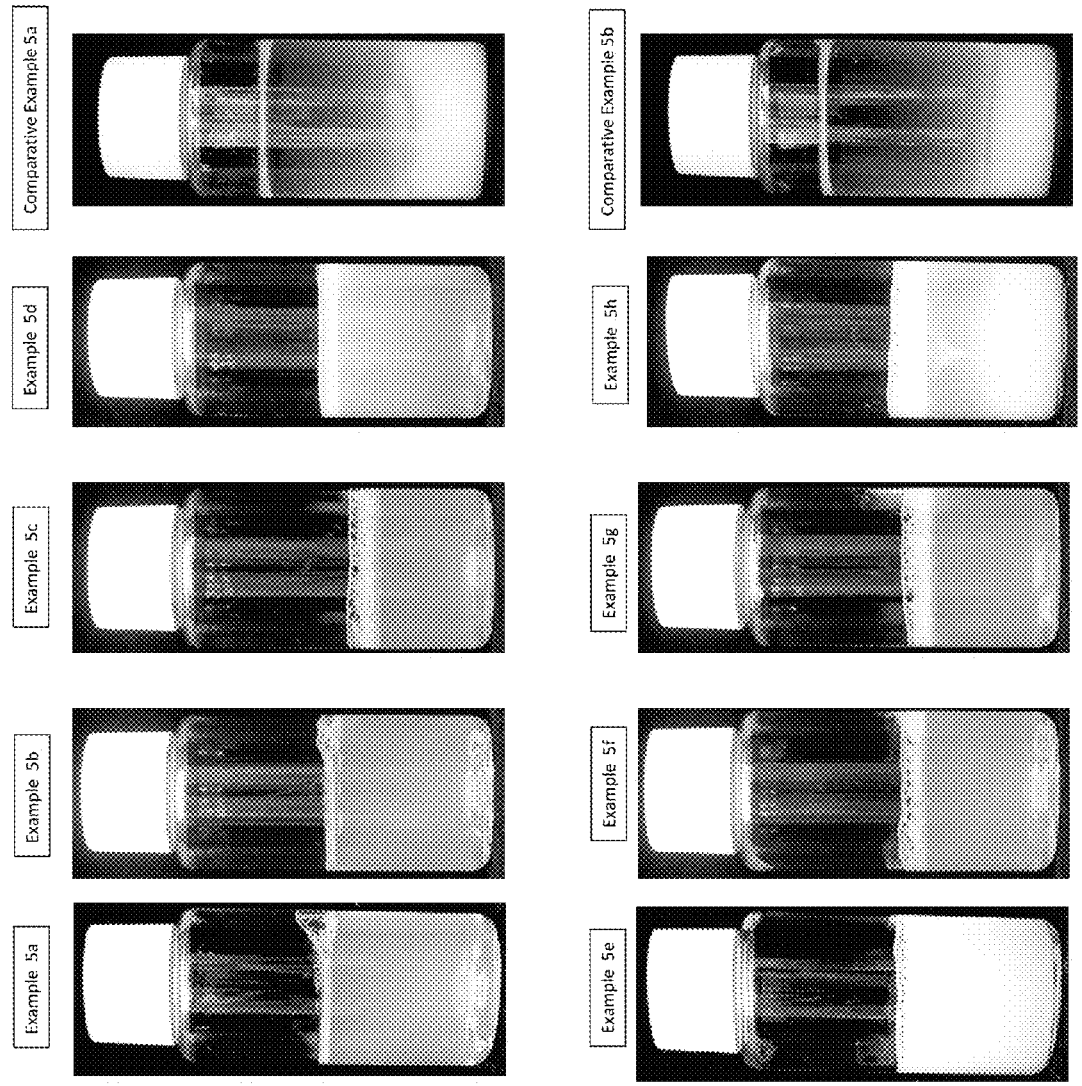
FIG. 4 shows photographs showing the dispersion state of Examples 5a to 5h and Comparative Examples 5a and 5b.
Figure 5:
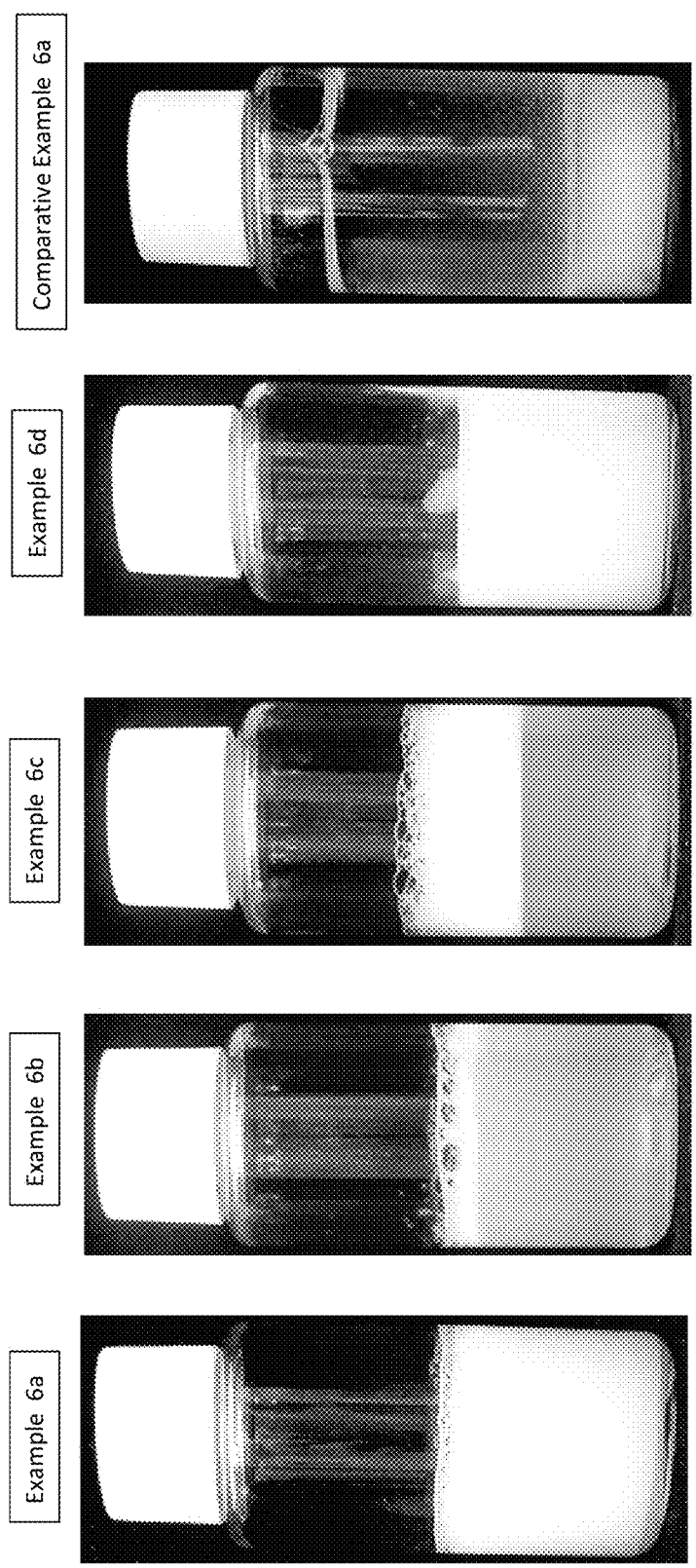
Figure 6:
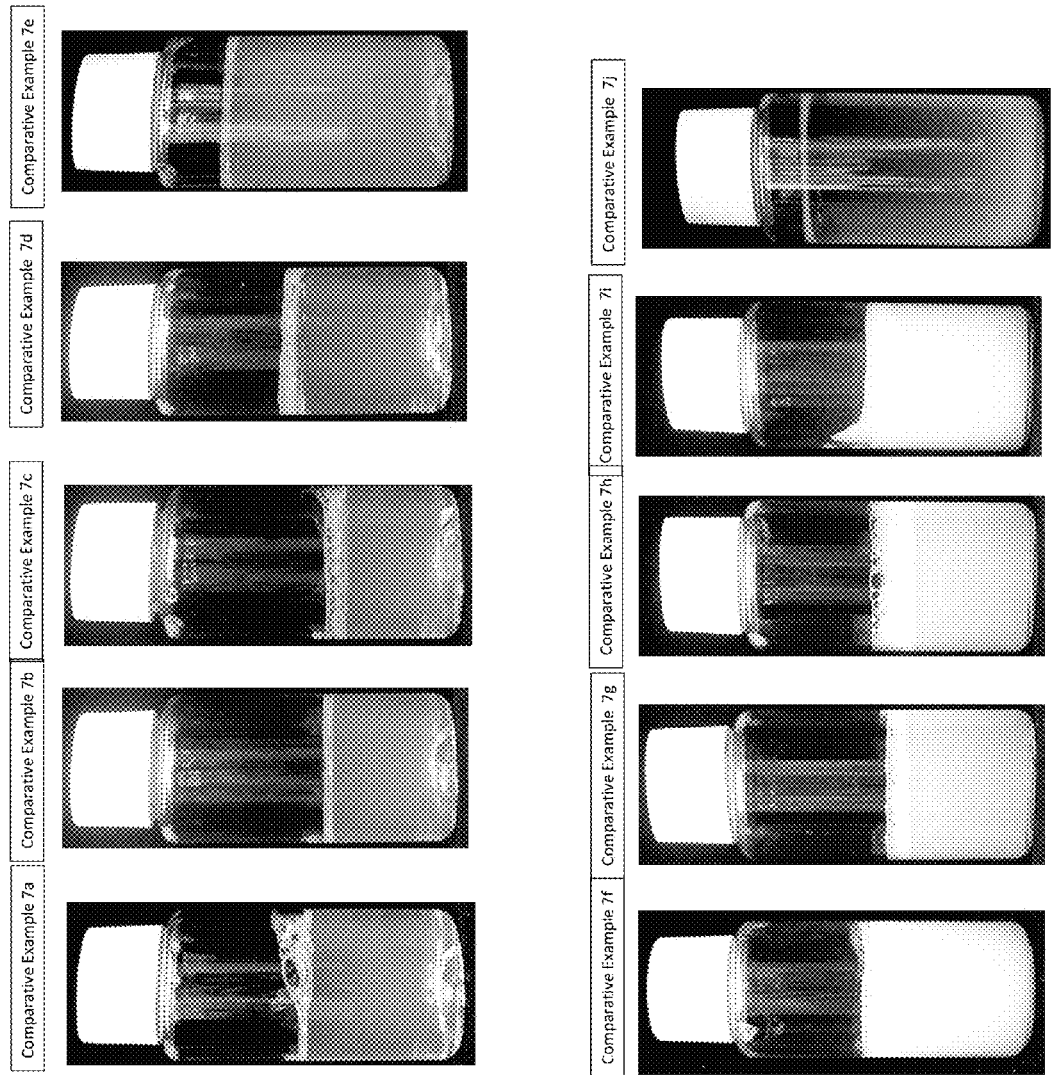
FIG. 6 shows photographs showing the dispersion state of Comparative Examples 7a to 7j.
Figure 7:
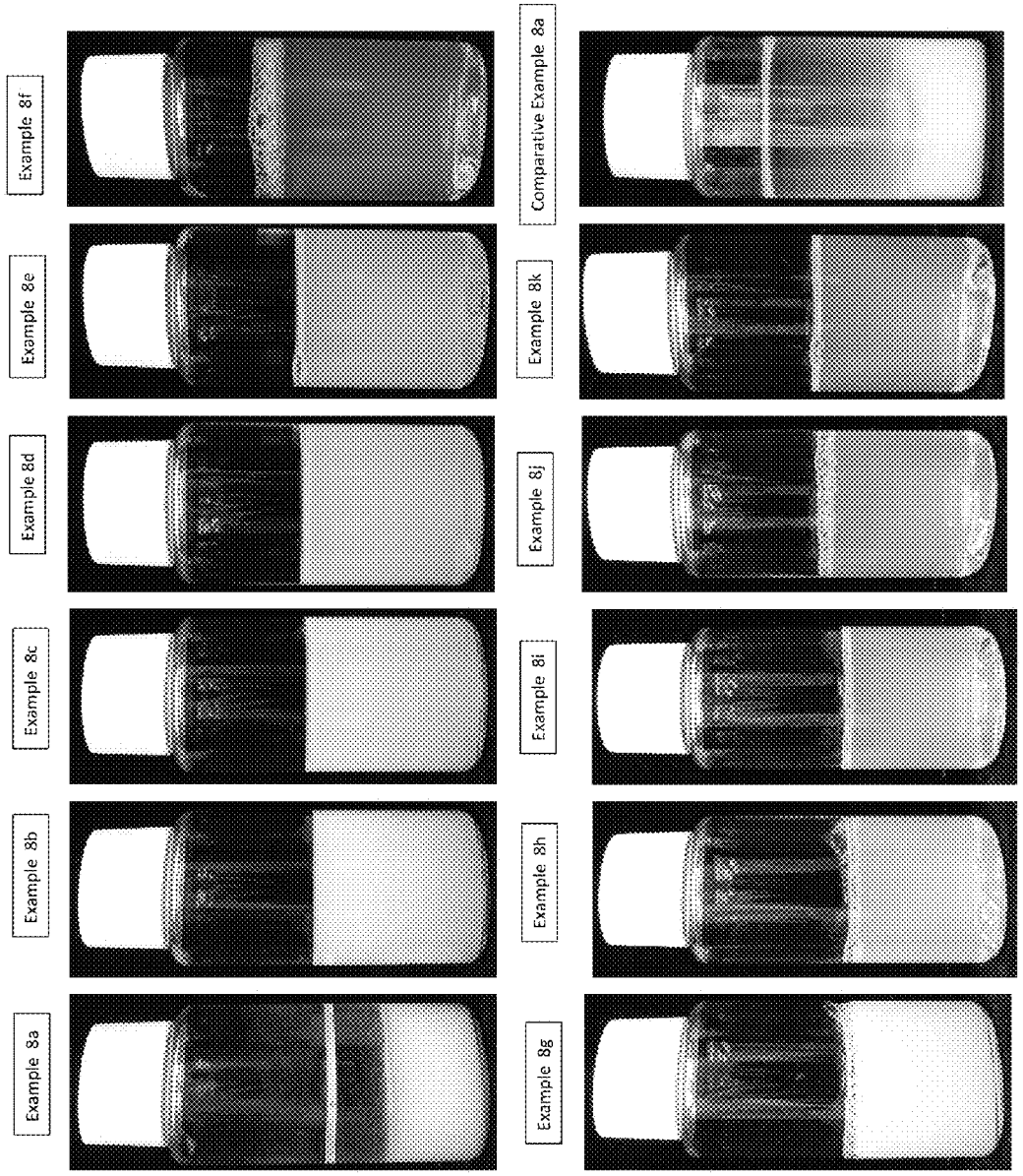
Figure 8:
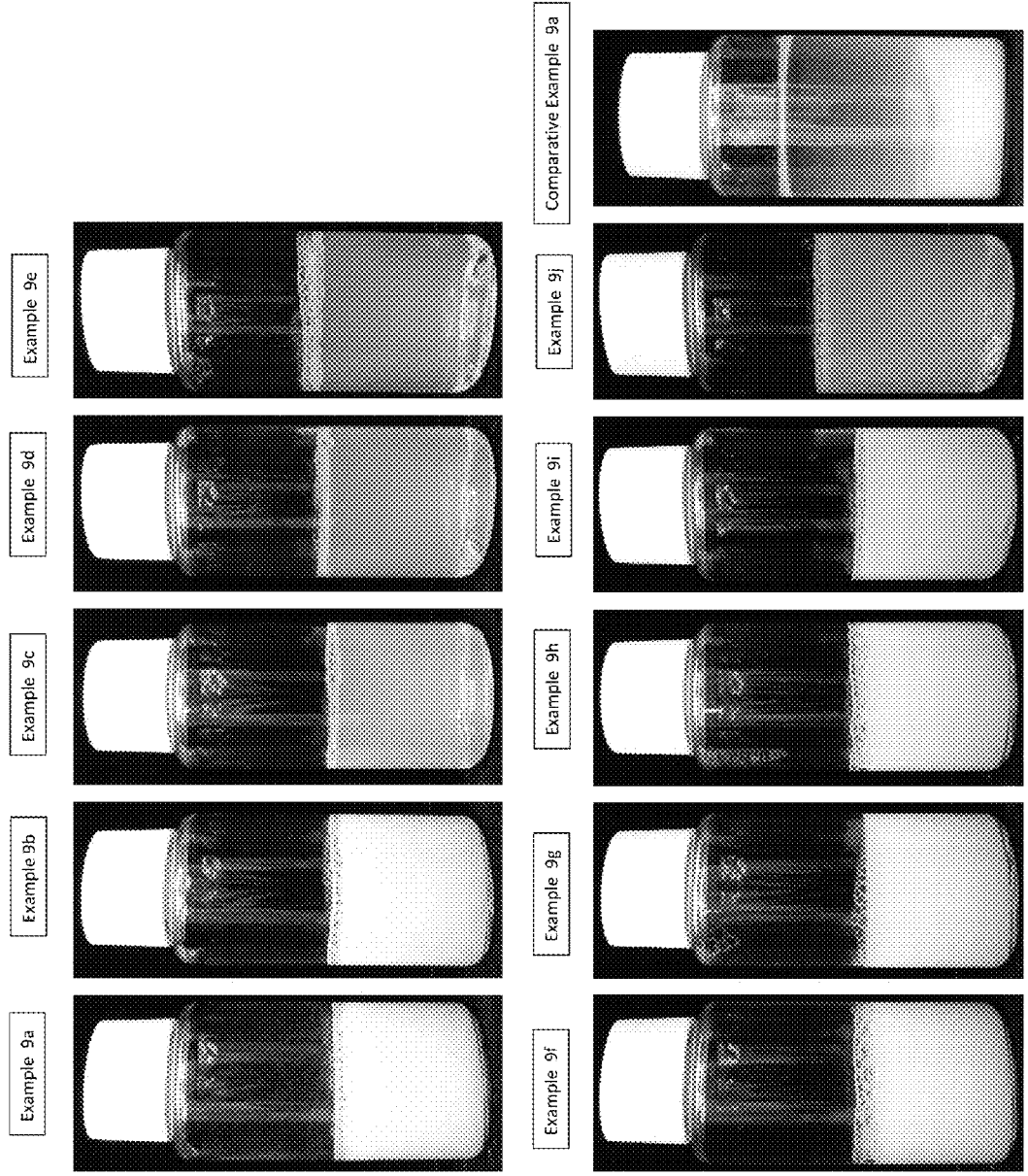

The hair treatment agent and the method for causing a modified peptide to penetrate into the hair related to the embodiments of the invention will be explained below by way of specific examples.

The hair treatment agent according to an embodiment is a hair treatment agent having a pH of from 3.5 to 5.5, and has (A) a predetermined modified peptide, and (B) an anionic surfactant incorporated therein. In regard to the hair treatment agent, water may be incorporated therein, and in a case in which water is incorporated, the amount of incorporation of water may be, for example, set to 65% by mass or more. Furthermore, a hair treatment agent obtainable by further incorporating materials that are known as raw materials of hair treatment agents as optional raw materials, may also be considered as the hair treatment agent of some embodiments.

(A) Modified Peptide

The hair treatment agent of some embodiments has a predetermined modified peptide incorporated therein. This predetermined modified peptide includes a main chain formed by peptide bonds of two or more amino acids, and side chain groups bonded to this main chain.

The main chain of the modified peptide is not particularly limited. An example of this main chain is a main chain that is identical with the main chain of a peptide containing cysteine as one of the constituent amino acids. Furthermore, examples of the peptide containing cysteine as one of the constituent amino acids include keratin and casein. Keratin is known as peptide having a high cysteine proportion among natural product-derived peptides, and keratin constitutes a raw material from which the relevant modified peptide is efficiently obtainable. From such a viewpoint, regarding the main chain of the modified peptide, a main chain that is identical with the main chain of keratin is suitable.

The predetermined modified peptide includes one kind or two or more kinds of side chain groups selected from a side chain group having a structure represented by the following Formula (I), a side chain group having a salt of a structure represented by the following Formula (I), a side chain group having a structure represented by the following Formula (II), a side chain group having a salt of a structure represented by the following Formula (II), a side chain group having a structure represented by the following Formula (III), and a side chain group having a salt of a structure represented by the following Formula (III):

$$-S-S-(CH_2)_n-COOH \qquad (I)$$

(wherein in Formula (I), n represents 1 or 2)

$$-S-S-CH(CH_3)-COOH \qquad (II)$$

$$-S-S-CH(COOH)-CH_2-COOH \qquad (III).$$

The salt of a structure represented by Formula (I), the salt of a structure represented by Formula (II), and the salt of a structure represented by Formula (III) are each an ion conjugate between a carboxylate anion and a cation. Examples of the unit that serves as the cation include ammonium such as $NH_4$; and metal atoms such as Na and K.

The modified peptide is such that as the molecular weight is smaller, the modified peptide can easily penetrate into the hair and is easily dispersible in the hair treatment agent in some embodiments. Therefore, as the molecular weight is smaller, when the pH of the hair treatment agent is decreased, the effect of the molecular weight exerted on the penetrability into the hair or the dispersibility in the hair treatment agent is small. Furthermore, as the molecular weight is larger, it is difficult for the modified peptide to penetrate into the hair in some embodiments, and the dispersibility obtainable when the pH of the composition is lowered is reduced. From this point of view, the molecular weight of the modified peptide may be 70,000 or less, preferably 50,000 or less, and more preferably 30,000 or less. The lower limit of the same molecular weight is not particularly limited; however, for example, the lower limit is 10,000. Here, in regard to the molecular weight of the modified peptide, the molecular weight calculated from the relative distance between the band of the modified peptide according to sodium dodecyl sulfate-polyacrylamide gel electrophoresis (SDS-PAGE) and the bands of molecular weight markers, is regarded as the molecular weight of the modified peptide and employed.

The lower limit of the amount of incorporation of the modified peptide in the hair treatment agent related to some embodiments is not particularly limited; however, from the viewpoint of enhancing the hair characteristics as a result of penetration of the modified peptide into the hair, for example, the lower limit may be 0.00001% by mass, preferably 0.0001% by mass, more preferably 0.001% by mass, and even more preferably 0.01% by mass. On the other hand, from the viewpoint of suppressing an increase in the cost caused by incorporation of large quantities and enhancing the transparency of the hair treatment agent, the upper limit of the amount of incorporation of the modified peptide may be 5% by mass, preferably 3% by mass, more preferably 2% by mass, and even more preferably 0.5% by mass.

The modified peptide in the hair treatment agent related to some embodiments can be produced by, for example, a known production method as disclosed in JP 5798741 B1.

(B) Anionic Surfactant

In the hair treatment agent of some embodiments, one kind or two or more kinds of anionic surfactants are incorporated. By incorporating anionic surfactants, hair penetrability of the modified peptide can be enhanced.

Examples of the anionic surfactant include a carboxylic acid-based anionic surfactant, a sulfonic acid-based anionic surfactant, a sulfuric acid-based anionic surfactant, and a phosphoric acid-based anionic surfactant.

(Carboxylic Acid-Based Anionic Surfactant)

Examples of the carboxylic acid-based anionic surfactant include a N-acyl amino acid salt, an alkyl ether carboxylic acid salt, a fatty acid amide ether carboxylic acid salt, and an acyl lactic acid salt.

Examples of the N-acyl amino acid salt include a N-acyl glutamate, a N-acyl aspartate, a N-acyl methylalanate, a N-acyl glycinate, a N-acyl prolinate, and a N-acyl sarcosinate.

Examples of the alkyl ether carboxylic acid salt include a polyoxyethylene lauryl ether acetate, a polyoxyethylene tridecyl ether acetate, and an alkyl glycol acetate.

Examples of the fatty acid amide ether carboxylic acid salt include a polyoxyethylene lauric acid amide ether carboxylate, a polyoxyethylene coconut oil fatty acid amide ether carboxylate, and a polyoxyethylene myristic acid amide ether carboxylate.

Examples of the acyl lactic acid salt include stearoyl lactate and isostearoyl lactate.

(Sulfonic Acid-Based Anionic Surfactant)

Examples of the sulfonic acid-based anionic surfactant include an alkane sulfonate, an α-olefin sulfonate, an α-sulfo fatty acid methyl ester salt, an acyl isethionate, an alkyl glycidyl ether sulfonate, an alkyl sulfosuccinate, an alkyl sulfoacetate, an alkyl benzenesulfonate, an alkyl naphthalenesulfonate, and a N-acyl methyltaurinate.

Examples of the alkane sulfonate include a sodium alkyl (C14-18) sulfonate.

Examples of the α-olefin sulfonate include a tetradecene sulfonate.

Examples of the α-sulfo fatty acid methyl ester salt include methyl-2-sulfolaurate and a polyoxyethylene fatty acid methyl ester.

Examples of the acyl isethionate include a lauroyl isethionate and a coconut oil fatty acid ethyl ester sulfonate.

Examples of the alkyl glycidyl ether sulfonate include an alkyl glyceryl sulfonate.

Examples of the alkyl sulfosuccinate include sulfosuccinic acid di(2-ethylhexyl) salt, sulfosuccinic acid lauryl salt, polyoxyethylene sulfosuccinic acid lauryl salt, polyoxyethylene alkyl (12-14) sulfosuccinate, and sulfosuccinic acid polyoxyethylene lauroyl ethanolamide salt.

Examples of the alkyl sulfoacetate include lauryl sulfoacetate.

Examples of the alkyl benzenesulfonate include dodecyl benzenesulfonate.

Examples of the alkyl naphthalenesulfonate include sodium methyl naphthalenesulfonate.

Examples of the N-acyl methyltaurinate include lauroyl methyltaurinate, coconut oil fatty acid methyltaurinate, myristoyl methyltaurinate, palmitoyl methyltaurinate, and stearoyl methyltaurinate.

(Sulfuric Acid-Based Anionic Surfactant)

Examples of the sulfuric acid-based anionic surfactant include an alkyl sulfate, an alkyl ether sulfate, an alkyl aryl ether sulfate, a fatty acid alkanolamide sulfate, and a fatty acid monoglyceride sulfate.

Examples of the alkyl sulfate include lauryl sulfate, myristyl sulfate, cetyl sulfate, and an alkyl (C11, 13, 15) sulfate.

Examples of the alkyl ether sulfate include polyoxyethylene lauryl ether sulfate, polyoxyethylene alkyl (12, 13) ether sulfate, polyoxyethylene alkyl (11, 12, 13, 14, 15) ether sulfate, and polyoxyethylene alkyl (12, 13, 14, 15) ether sulfate.

Examples of the alkyl aryl ether sulfate include polyoxyethylene nonyl phenyl ether sulfate.

Examples of the fatty acid alkanolamide sulfate include polyoxyethylene alkyl coconut oil fatty acid monoethanolamide sulfate.

Examples of the fatty acid monoglyceride sulfate include hardened coconut oil fatty acid glyceryl sulfate.

(Phosphoric Acid-Based Anionic Surfactant)

Examples of the phosphoric acid-based anionic surfactant include an alkyl phosphate, a polyoxyalkylene alkyl ether phosphate, an alkyl aryl ether phosphate, and a fatty acid amide ether phosphate.

Examples of the alkyl phosphate include lauryl phosphate and cetyl phosphate.

Examples of the polyoxyalkylene alkyl ether phosphate include polyoxyethylene lauryl ether phosphate, polyoxyethylene alkyl (C12-15) ether phosphate, polyoxyethylene cetyl ether phosphate, polyoxyethylene oleyl ether phosphate, and polyoxyethylene stearyl ether phosphate.

Examples of the alkyl aryl ether phosphate include polyoxyethylene nonyl phenyl ether phosphate.

Examples of the fatty acid amide ether phosphate include polyoxyethylene alkyl monoethanol amide phosphate.

From the viewpoint of sufficiently enhancing the hair penetrability of the modified peptide, it is preferable to incorporate, among the anionic surfactants, any one kind or two or more kinds of an alkyl ether sulfate, an alkyl ether carboxylate, an α-olefin sulfonate, and a N-acyl amino acid salt.

Meanwhile, from the viewpoint of further enhancing the hair penetrability of the modified peptide and the dispersibility of the modified peptide in the hair treatment agent, it is particularly preferable to incorporate any one kind or two or more kinds of an alkyl ether sulfate, an alkyl ether carboxylate, and an α-olefin sulfonate.

The amount of incorporation of the anionic surfactant in the hair treatment agent of some embodiments is not particularly limited; however, in order to manifest enhancement of the hair penetrability and dispersibility of the modified peptide, the amount of incorporation of the anionic surfactant is desirably from 1 part by mass to 30 parts by mass, and preferably from 3 parts by mass to 15 parts by mass, relative to 1 part by mass of the modified peptide. The lower limit of the amount of incorporation of the anionic surfactant in the hair treatment agent is not particularly limited; however, the amount of incorporation is desirably 0.00001% by mass or more, preferably 0.0001% by mass or more, more preferably 0.001% by mass or more, and even more preferably 0.01% by mass or more. Furthermore, the upper limit of the amount of incorporation of the anionic surfactant in the hair treatment agent is desirably 30% by mass or less, preferably 20% by mass or less, and more preferably 10% by mass or less.

Particularly, in a case in which an alkyl ether sulfate is incorporated as the anionic surfactant into the hair treatment agent, from the viewpoint of obtaining both an effect of enhancing hair penetrability of the modified peptide and an effect of enhancing dispersibility of the modified peptide in the hair treatment agent, the pH of the hair treatment agent is preferably from 3.5 to 5.5, and more preferably from 4.0 to 5.5. Furthermore, in this case, the mixing proportion of the alkyl ether sulfate in the hair treatment agent is preferably from 1% by mass to 30% by mass, and more preferably from 3% by mass to 20% by mass.

Particularly, in a case in which an alkyl ether carboxylate is incorporated as the anionic surfactant into the hair treatment agent, from the viewpoint of obtaining both an effect of enhancing hair penetrability of the modified peptide and an effect of enhancing dispersibility of the modified peptide in the hair treatment agent, the pH of the hair treatment agent is preferably from 4.0 to 5.5, and more preferably from 4.5 to 5.5. Furthermore, in this case, the mixing proportion of the alkyl ether carboxylate in the hair treatment agent is preferably from 2% by mass to 30% by mass, more preferably from 3% by mass to 20% by mass, and particularly preferably from 7% by mass to 15% by mass.

Particularly, in a case in which an α-olefin sulfonate is incorporated as the anionic surfactant into the hair treatment agent, from the viewpoint of obtaining both an effect of enhancing hair penetrability of the modified peptide and an effect of enhancing dispersibility of the modified peptide in the hair treatment agent, the pH of the hair treatment agent is preferably from 3.5 to 5.5, and more preferably from 4.0 to 5.5. Furthermore, in this case, the mixing proportion of the α-olefin sulfonate in the hair treatment agent is preferably from 0.5% by mass to 30% by mass, more preferably from 1% by mass to 20% by mass, and particularly preferably from 3% by mass to 15% by mass.

Particularly, in a case in which a N-acyl amino acid salt is incorporated as the anionic surfactant into the hair treatment agent, from the viewpoint of obtaining both an effect of enhancing hair penetrability of the modified peptide and an effect of enhancing dispersibility of the modified peptide in the hair treatment agent, the pH of the hair treatment agent is preferably from 4.5 to 5.5, and more preferably from 4.7 to 5.5. Furthermore, in this case, the mixing proportion of the N-acyl amino acid salt in the hair treatment agent is preferably from 4% by mass to 30% by mass, and more preferably from 5% by mass to 20% by mass.

(Optional Raw Materials)

Optional raw materials that are incorporated into the hair treatment agent of some embodiments are appropriately selected from materials that are known as raw materials of treatment agents for hair. Examples of these optional raw materials include cationic surfactants, amphoteric surfactants, nonionic surfactants, higher alcohols, polyhydric alcohols, lower alcohols, saccharides, ester oils, oils and fats, fatty acids, hydrocarbons, waxes, silicones, polymer compounds, amino acids, animal and plant extracts, microbial-derived products, inorganic compounds, fragrances, preservatives, chelating agents, and ultraviolet absorbers.

(pH)

The pH of the hair treatment agent of some embodiments is from 3.5 to 5.5 under the conditions of 25° C. Even if the pH is set to be lower, since an anionic surfactant has been incorporated, decrease in the dispersibility of the modified peptide is suppressed, and stability of the hair treatment agent of some embodiments can be promoted. A pH value preferable for enhancing hair penetrability and dispersibility of the modified peptide is from 4.0 to 5.5, and particularly preferably from 4.5 to 5.5.

(Viscosity)

The viscosity of the hair treatment agent of some embodiments is not particularly limited. This viscosity is, for example, 1,000 mPa·s or less. Even with such a low viscosity, decrease in the dispersibility of the modified peptide is suppressed. Meanwhile, the viscosity described above means a value obtainable by initiating measurement using a B-type viscometer and using an appropriate rotor at a speed of rotor rotation of 12 rpm at 25° C., and taking the measurement data 60 seconds after the initiation of measurement.

(Applications)

The hair treatment agent of some embodiments is appliable on the hair in order to cause a modified peptide to penetrate into the internal structure of the hair. In a case in which the hair treatment agent of some embodiments is used by applying the agent on the hair, the hair treatment agent may be a formulation produced without incorporating the optional raw materials described above, or may be a formulation incorporated with the optional raw materials. Examples of the formulation form that can be employed when the hair treatment agent in some embodiments is used include a liquid, a cream, a gel, a foam (froth), and a spray.

The hair treatment agent of the embodiments may be used as, for example, a shampoo, a conditioner (for example, a conditioner that is not washed away, a conditioner that is washed away, a conditioner that is combinedly used for hairdressing, one constituent agent for a multi-agent type conditioner, a conditioner for a preliminary treatment for a perm, a conditioner for a post-treatment for a perm, a conditioner for a preliminary treatment for hair coloring, a conditioner for a post-treatment for hair coloring, a conditioner for a preliminary treatment for bleaching, or a conditioner for a post-treatment for bleaching), or a hairdressing agent.

The raw materials that are used in the case of producing the hair treatment agent of the embodiments can be appropriately selected from, for example, materials known as raw materials of hair treatment agents. Examples of these raw materials include cationic surfactants, amphoteric surfactants, nonionic surfactants, higher alcohols, polyhydric alcohols, lower alcohols, saccharides, ester oils, oils and fats, fatty acids, hydrocarbons, waxes, silicones, polymer compounds, amino acids, animal and plant extracts, microbial-derived products, inorganic compounds, fragrances, preservatives, chelating agents, and ultraviolet absorbers.

EXAMPLES

Hereinafter, the embodiments of the invention will be described in detail based on Examples; however, the embodiments are not intended to be limitedly construed based on the description of these Examples.

(Modified Peptide (I) Liquid)

A transparent modified peptide (I) liquid in which a modified peptide having a side chain group (n=1) represented by Formula (I) described above was dispersed was obtainable according to the following reduction step, oxidizing agent mixing step, solid-liquid separation step, collecting step, hydrolysis step, and preparation step.

Reduction Step:

Merino wool that had been washed with a neutral detergent and dried was cut to a length of about 5 mm 5.0 parts by mass of this wool, 15.4 parts by mass of a 30 mass % aqueous solution of sodium thioglycolate, and 8.5 parts by mass of a 6 mol/L aqueous solution of sodium hydroxide were mixed, and water was further mixed into the mixture. Thus, a liquid to be treated at pH 11 was prepared in a total amount of 150 parts by mass. This liquid to be treated was stirred under the conditions of 45° C. for 1 hour. Subsequently, water was further mixed into the liquid to be treated, so as to adjust the total amount to 200 parts by mass, and the final mixture was left to stand under the conditions of 45° C. for 2 hours. Subsequently, the mixture was naturally cooled until the liquid temperature reached normal temperature.

Oxidizing Agent Mixing Step:

While the liquid to be treated obtainable after the reduction step was stirred, 178 parts by mass of an aqueous solution in which 15.26 parts by mass of 35 mass % aqueous hydrogen peroxide was incorporated, was mixed with the relevant liquid while being stirred for about 30 minutes (the pH of the liquid to be treated increased along with the mixing of aqueous hydrogen peroxide; however, this increase was adjusted to a pH in the range of 10 to 11 by mixing the liquid to be treated with an about 20 mass % aqueous solution of acetic acid). Thereafter, an about 20 mass % aqueous solution of acetic acid was slowly mixed into the mixture, and the pH of the liquid to be treated was gradually adjusted from 11 to 7.

Solid-Liquid Separation Step and Collecting Step:

The liquid obtainable from the oxidizing agent mixing step was filtered, and thereby, insoluble materials in the liquid were removed. Thereafter, 160 parts by mass of an aqueous solution having 97.2 parts by mass of a 36 mass % of an aqueous solution of hydrochloric acid incorporated therein was added to the collected liquid portion (filtrate), and thereby the pH of the liquid was adjusted from 7 to 3.8.

Thus, modified peptide (I) was caused to precipitate. This precipitate was collected and washed with water, and thus modified peptide (I) in a solid form was obtainable.

Hydrolysis Step:

An aqueous solution prepared by incorporating the solid modified peptide (I) obtainable in the collecting step, and adjusting the pH to 10.5 with 2-amino-2-methyl-1-propanol, was heated for 2 hours at 80° C. This aqueous solution after heating was filtered, and a filtrate was obtainable.

Preparation Step:

The filtrate obtainable in the hydrolysis step, phenoxyethanol, 1,3-butylene glycol, betaine lauryldimethylaminoacetate, and water were mixed, and a modified peptide (I) liquid was obtainable. The relevant liquid includes 1% by mass of the modified peptide (I), 1% by mass of phenoxyethanol, 3% by mass of 1,3-butylene glycol, and 3% by mass of betaine lauryldimethylaminoacetate, and in an evaluation based on SDS-PAGE, it was recognized that the band of the modified peptide (I) corresponded to a molecular weight of 44,000.

(Hair Penetrability)

An evaluation on the hair penetrability of the modified peptide (I) was carried out according to the evaluation method and evaluation criteria described below.

(Evaluation Method)

Penetrability of a hair treatment agent including the modified peptide (I) liquid into the hair was evaluated according to the following procedure of steps (1) to (6).

(1) FTSC-MES is added to the modified peptide (I) liquid, and unreacted FTSC is removed using a gel filtration column. Subsequently, a FTSC-MES-added modified peptide liquid is obtainable. This FTSC-MES is produced as follows. A 0.2M aqueous solution of NaOH is added dropwise to a liquid obtainable by dissolving 1.065 parts by mass of 2-(N-morpholino)ethanesulfonic acid (MES) in 40 parts by mass of water, and thereby an aqueous solution of MES at pH 5.5 is prepared. 0.00042 parts by mass of a fluorescent dye, Fluorescein-5-thiosemicarbazide (FTSC), is dissolved in the aqueous solution of MES, and water is added thereto to adjust the total amount to about 50 parts by mass. Thus, FTSC-MES is prepared. (2) A liquid obtainable by adding various anionic surfactants to the FTSC-MES-added modified peptide liquid, and a FTSC-MES-added modified peptide liquid without any anionic surfactant added thereto are respectively prepared, and the pH of these liquids is adjusted to a predetermined value using citric acid and 2-amino-2-methyl-1-propanol. (3) A hair sample is shampooed, and then washed with ethanol and water. (4) The hair washed in step (3) is immersed for 30 minutes in each of the aqueous solutions of the modified peptide prepared in step (2), and then the hair is washed with water and dried at room temperature. (5) The dried hair is cut at the root part with a microtome. (6) The cut surface of the hair is observed by fluorescence microscopy (excited light wavelength: 340 nm).

In regard to the fluorescence microscopic observation in the procedure of step (6), if fluorescence can be recognized up to the center portion of the hair on the inner side of hair cuticle, hair penetrability of the modified peptide (I) can be confirmed. When fluorescence can be observed up to the center portion of the hair, this indicates excellent hair penetrability.

(Evaluation Criteria)

Excellent: Fluorescence is clearly recognizable in the vicinity of the hair core, as compared to the reference.

Good: Fluorescence is recognizable in the vicinity of the hair core, as compared to the reference.

Same: Fluorescence in the vicinity of the hair core is almost equal to the reference.

Poor: Fluorescence in the vicinity of the hair core is slightly poor compared to the reference.

Very poor: Fluorescence in the vicinity of the hair core is clearly poor compared to the reference.

Hair treatment agents each prepared by incorporating sodium polyoxyethylene(4.5) lauryl ether acetate and water into the FTSC-MES-added modified peptide liquid, and adjusting the pH with citric acid and 2-amino-2-methyl-1-propanol, were produced as indicated in the following Table 1. As an object of comparison, a hair treatment agent that did not have any anionic surfactant incorporated therein was produced (Comparative Example 1c). The results of an evaluation of penetrability of those hair treatment agents are presented. Also, FIG. 1 shows fluorescence microscopic observation photographs of Examples 1a to 1d and Comparative Examples 1a to 1c.

TABLE 1

| | Example 1a | Example 1b | Example 1c | Example 1d | Comparative Example 1a | Comparative Example 1b | Comparative Example 1c |
|---|---|---|---|---|---|---|---|
| FTSC-MES-added modified peptide (I) | 1 | 1 | 1 | 1 | 1 | 1 | 1 |
| Sodium polyoxyethylene(4.5) lauryl ether acetate | 10 | 10 | 10 | 10 | 10 | 10 | — |
| pH | 3.5 | 4.0 | 4.5 | 5.0 | 6.5 | 9.0 | 6.5 |
| Penetrability into hair | Excellent | Excellent | Excellent | Excellent | Same | Poor | Reference |

Amount of Incorporation: Mass Ratio

It can be seen that the FTSC-MES-added modified peptide (I) prepared by incorporating sodium polyoxyethylene (4.5) lauryl ether acetate, which is an anionic surfactant, has enhanced penetrability into the hair at a pH 3.5 to 5.0, as compared to the reference (Comparative Example 1c: no anionic surfactant incorporated).

Next, hair treatment agents were produced by incorporating various anionic surfactants (sodium polyoxyethylene(2) lauryl ether sulfate, sodium N-coconut oil fatty acid acyl-L-glutamate, sodium tetradecene sulfonate, and sodium polyoxyethylene(4.5) lauryl ether acetate) and water into the FTSC-MES-added modified peptide (I) liquid, and adjusting the pH to 4.7. As an object of comparison, a hair treatment agent that did not have any anionic surfactant incorporated therein was produced (Comparative Example 2a). The results of an evaluation of penetrability of these hair treatment agents produced as indicated in the following Table 2 are presented.

TABLE 2

|  | Example 2a | Example 2b | Example 2c | Example 2d | Comparative Example 2a |
|---|---|---|---|---|---|
| FTSC-MES-added modified peptide (I) | 1 | 1 | 1 | 1 | 1 |
| Sodium polyoxyethylene(4.5) lauryl ether acetate | 10 | — | — | — | — |
| Sodium tetradecene sulfonate | — | 10 | — | — | — |
| Sodium polyoxyethylene(2) lauryl ether sulfate | — | — | 10 | — | — |
| Sodium N-coconut oil fatty acid acyl-L-glutamate | — | — | — | 10 | — |
| pH | 4.7 | 4.7 | 4.7 | 4.7 | 4.7 |
| Hair penetrability | Excellent | Good | Good | Good | Reference |

Amount of Incorporation: Mass Ratio

It can be seen that FTSC-MES-added modified peptide (I) mixed with various anionic surfactants have enhanced penetrability into the hair, as compared to the reference (Comparative Example 2a: no anionic surfactant incorporated).

Furthermore, a hair treatment agent prepared by incorporating sodium polyoxyethylene(4.5) lauryl ether acetate as an anionic surfactant and water into the FTSC-MES-added modified peptide liquid, and adjusting the pH to 4.5, was produced as indicated in the following Table 3 (Example 3a). As an object of comparison, a hair treatment agent prepared by incorporating cetyltrimethylammonium chloride as a cationic surfactant instead of an anionic surfactant, together with water, and similarly adjusting the pH to 4.5, was produced as indicated in the following Table 3 (Comparative Example 3a). Meanwhile, in order to compare penetrability while having the dispersibility of Example 3a and Comparative Example 3a adjusted to the same extent, the amount of incorporation of cetyltrimethylammonium chloride of Comparative Example 3a was adjusted so as to be slightly lower. The results of evaluation of penetrability of these hair treatment agents are presented. The evaluation criteria were the same as those for Table 1, and Example 3a was evaluated based on Comparative Example 3a as a reference. Furthermore, fluorescence microscopic observation photographs of Example 3a and Comparative Example 3a are shown in FIG. 2.

TABLE 3

|  | Example 3a | Comparative Example 3a |
|---|---|---|
| FTSC-MES-added modified peptide (I) | 1 | 1 |
| Sodium polyoxyethylene(4.5) lauryl ether acetate | 10 | — |
| Cetyltrimethylammonium chloride | — | 5 |
| pH | 4.5 | 4.5 |
| Penetrability into hair | Excellent | Reference |

Amount of Incorporation: Mass Ratio

It can be seen that the FTSC-MES-added modified peptide (I) having an anionic surfactant incorporated therein has enhanced penetrability into the hair as compared to the reference (Comparative Example 3a), into which a cationic surfactant has been incorporated instead of an anionic surfactant.

(Dispersibility and pH)

Dispersibility of the modified peptide (I) was evaluated based on the presence or absence of incorporation of an anionic surfactant and the difference of pH. Hair treatment agents were produced by incorporating various anionic surfactants (sodium polyoxyethylene(4.5) lauryl ether acetate, sodium tetradecene sulfonate, sodium polyoxyethylene(2) lauryl ether sulfate, and sodium N-coconut oil fatty acid acyl-L-glutamate) and water into the modified peptide (I) liquid, and adjusting the pH to a predetermined value using citric acid and 2-amino-2-methyl-1-propanol. As an object of comparison, a hair treatment agent that did not have any anionic surfactant incorporated therein was produced. The evaluation method and the evaluation criteria were as described below.

(Evaluation Method)

A hair treatment agent prepared by incorporating the modified peptide and an anionic surfactant and adjusting the pH to a predetermined value was introduced into a transparent vessel and was left to stand. Subsequently, dispersibility of the modified peptide (I) in the hair treatment agent was evaluated by visual inspection based on the external appearance.

(Evaluation Criteria)

Good: The modified peptide is uniformly dispersed without becoming cloudy.

Medium: The modified peptide is uniformly dispersed with some cloudiness.

Poor: Cloudiness or precipitation occurs, and the modified peptide is not uniformly dispersed.

The results for an evaluation of dispersibility of the modified peptide (I) in the hair treatment agents prepared as indicated in the following Table 4, the hair treatment agents having the pH adjusted to 5.5 or 5.0, are shown below.

TABLE 4

|  | Example 4a | Example 4b | Example 4c | Example 4d | Comparative Example 4a | Example 4e | Example 4f | Example 4g | Example 4h | Comparative Example 4b |
|---|---|---|---|---|---|---|---|---|---|---|
| Modified peptide (I) | 1 | 1 | 1 | 1 | 1 | 1 | 1 | 1 | 1 | 1 |
| Sodium polyoxyethylene(4.5) lauryl ether acetate | 9 | — | — | — | — | 9 | — | — | — | — |

TABLE 4-continued

| | Example 4a | Example 4b | Example 4c | Example 4d | Comparative Example 4a | Example 4e | Example 4f | Example 4g | Example 4h | Comparative Example 4b |
|---|---|---|---|---|---|---|---|---|---|---|
| Sodium tetradecene sulfonate | — | 5 | — | — | — | — | 5 | — | — | — |
| Sodium polyoxyethylene(2) lauryl ether sulfate | — | — | 5 | — | — | — | — | 5 | — | — |
| Sodium N-coconut oil fatty acid acyl-L-glutamate | — | — | — | 5 | — | — | — | — | 5 | — |
| pH | 5.5 | 5.5 | 5.5 | 5.5 | 5.5 | 5 | 5 | 5 | 5 | 5 |
| Dispersibility | Good | Good | Good | Good | Medium | Good | Good | Good | Good | Poor |

Amount of Incorporation: Mass Ratio

In Comparative Example 4a that did not have any anionic surfactant incorporated therein, cloudiness was observed. However, it was confirmed that in Examples 4a to 4d in which various anionic surfactants were incorporated, dispersibility of the modified peptide (I) increased. Furthermore, precipitation was observed in Comparative Example 4b; however, it was confirmed that in Examples 4e to 4h in which various anionic surfactants were incorporated, dispersibility of the modified peptide (I) increased.

The results for an evaluation of dispersibility of the modified peptide (I) in the hair treatment agents prepared as indicated in the following Table 5, the hair treatment agents having the pH adjusted to 4.5 or 4.0, are shown below.

TABLE 5

| | Example 5a | Example 5b | Example 5c | Example 5d | Comparative Example 5a | Example 5e | Example 5f | Example 5g | Example 5h | Comparative Example 5b |
|---|---|---|---|---|---|---|---|---|---|---|
| Modified peptide (I) | 1 | 1 | 1 | 1 | 1 | 1 | 1 | 1 | 1 | 1 |
| Sodium polyoxyethylene(4.5) lauryl ether acetate | 9 | — | — | — | — | 9 | — | — | — | — |
| Sodium tetradecene sulfonate | — | 5 | — | — | — | — | 5 | — | — | — |
| Sodium polyoxyethylene(2) lauryl ether sulfate | — | — | 5 | — | — | — | — | 5 | — | — |
| Sodium N-coconut oil fatty acid acyl-L-glutamate | — | — | — | 5 | — | — | — | — | 5 | — |
| pH | 4.5 | 4.5 | 4.5 | 4.5 | 4.5 | 4 | 4 | 4 | 4 | 4 |
| Dispersibility | Good | Good | Good | Medium | Poor | Medium | Good | Medium | Poor | Poor |

Amount of Incorporation: Mass Ratio

In Comparative Example 5a that did not have any anionic surfactant incorporated therein, precipitation was observed. However, it was confirmed that in Examples 5a to 5d in which various anionic surfactants were incorporated, dispersibility of the modified peptide (I) increased. Furthermore, precipitation was observed in Comparative Example 5b; however, it was confirmed that in Examples 5e to 5g in which anionic surfactants such as sodium polyoxyethylene (4.5) lauryl ether acetate, sodium tetradecene sulfonate, and sodium polyoxyethylene(2) lauryl ether sulfate were incorporated, dispersibility of the modified peptide (I) increased.

The results for an evaluation of the dispersibility of the modified peptide (I) in the hair treatment agents as indicated in the following Table 6, the hair treatment agents having the pH adjusted to 3.5, are presented below.

TABLE 6

| | Example 6a | Example 6b | Example 6c | Example 6d | Comparative Example 6a |
|---|---|---|---|---|---|
| Modified peptide (I) | 1 | 1 | 1 | 1 | 1 |
| Sodium polyoxyethylene(4.5) lauryl ether acetate | 9 | — | — | — | — |

TABLE 6-continued

|  | Example 6a | Example 6b | Example 6c | Example 6d | Comparative Example 6a |
|---|---|---|---|---|---|
| Sodium tetradecene sulfonate | — | 5 | — | — | — |
| Sodium polyoxyethylene(2) lauryl ether sulfate | — | — | 5 | — | — |
| Sodium N-coconut oil fatty acid acyl-L-glutamate | — | — | — | 5 | — |
| pH | 3.5 | 3.5 | 3.5 | 3.5 | 3.5 |
| Dispersibility | Poor | Medium | Medium | Poor | Poor |

Amount of Incorporation: Mass Ratio

In Comparative Example 6a that did not have any anionic surfactant incorporated therein, precipitation of the modified peptide (I) was observed. However, it was confirmed that in Examples 6b and 6c in which anionic surfactants such as sodium tetradecene sulfonate and sodium polyoxyethylene (2) lauryl ether sulfate were incorporated, dispersibility of the modified peptide (I) increased.

The results for an evaluation of dispersibility of the modified peptide (I) in the hair treatment agents as indicated in the following Table 7, the hair treatment agents having the pH adjusted to 6.5 or 3.0, are presented below.

TABLE 7

|  | Comparative Example 7a | Comparative Example 7b | Comparative Example 7c | Comparative Example 7d | Comparative Example 7e |
|---|---|---|---|---|---|
| Modified peptide (I) | 1 | 1 | 1 | 1 | 1 |
| Sodium polyoxyethylene(4.5) lauryl ether acetate | 9 | — | — | — | — |
| Sodium tetradecene sulfonate | — | 5 | — | — | — |
| Sodium polyoxyethylene(2) lauryl ether sulfate | — | — | 5 | — | — |
| Sodium N-coconut oil fatty acid acyl-L-glutamate | — | — | — | 5 | — |
| pH | 6.5 | 6.5 | 6.5 | 6.5 | 6.5 |
| Dispersibility | Good | Good | Good | Good | Good |

|  | Comparative Example 7f | Comparative Example 7g | Comparative Example 7h | Comparative Example 7i | Comparative Example 7j |
|---|---|---|---|---|---|
| Modified peptide (I) | 1 | 1 | 1 | 1 | 1 |
| Sodium polyoxyethylene(4.5) lauryl ether acetate | 9 | — | — | — | — |
| Sodium tetradecene sulfonate | — | 5 | — | — | — |
| Sodium polyoxyethylene(2) lauryl ether sulfate | — | — | 5 | — | — |
| Sodium N-coconut oil fatty acid acyl-L-glutamate | — | — | — | 5 | — |
| pH | 3 | 3 | 3 | 3 | 3 |
| Dispersibility | Poor | Poor | Poor | Poor | Poor |

Amount of Incorporation: Mass Ratio

It was confirmed that at pH 6.5, there was no change in the dispersibility of the modified peptide (I), irrespective of the presence or absence of the incorporation of anionic surfactants (Comparative Examples 7a to 7e). Furthermore, at pH 3.0, precipitation of the modified peptide (I) was observed, irrespective of the presence or absence of the incorporation of anionic surfactants (Comparative Examples 7f to 7j).

As can be seen from the results of Tables 4 to 7, when anionic surfactants are incorporated at a pH in the range of 3.0 to 6.5, dispersibility of the modified peptide (I) remains the same, or an increase in dispersibility is observed, as compared to the cases in which anionic surfactants are not incorporated. It is understood that at pH 5.5 to 4.5, dispersibility of the modified peptide (I) is increased in all of the hair treatment agents having anionic surfactants incorporated therein. Furthermore, at pH 4.0 and 3.5, an increase in dispersibility of the modified peptide (I) is observed in the cases in which sodium tetradecene sulfonate and sodium polyoxyethylene(2) lauryl ether sulfate, which are anionic surfactants, are incorporated.

(Dispersibility and Mixing Proportion of Anionic Surfactant)

Dispersibility of the modified peptide (I) was evaluated on the basis of the difference in the mixing proportions of anionic surfactants. Hair treatment agents were produced by incorporating various anionic surfactants and water into the modified peptide (I) liquid, and adjusting the pH to 4.5 using citric acid and 2-amino-2-methyl-1-propanol. As an object of comparison, a hair treatment agent that did not have any anionic surfactant incorporated therein was produced. The same evaluation method and the same evaluation criteria as those used for Tables 4 to 7 described above were employed. The evaluation results for dispersibility are presented in Tables 8 and 9.

The results for an evaluation of dispersibility of the modified peptide (I) in the hair treatment agents prepared as indicated in the following Table 8, the hair treatment agents having sodium polyoxyethylene(4.5) lauryl ether acetate or sodium tetradecene sulfonate incorporated therein as an anionic surfactant, are presented below.

TABLE 8

|  | Example 8a | Example 8b | Example 8c | Example 8d | Example 8e | Example 8f |
|---|---|---|---|---|---|---|
| Modified peptide (I) | 1 | 1 | 1 | 1 | 1 | 1 |
| Sodium polyoxyethylene(4.5) lauryl ether acetate | 1.5 | 2.5 | 3 | 3.5 | 4 | 9 |
| Sodium tetradecene sulfonate | — | — | — | — | — | — |
| Sodium polyoxyethylene(2) lauryl ether sulfate | — | — | — | — | — | — |
| Sodium N-coconut oil fatty acid acyl-L-glutamate | — | — | — | — | — | — |
| pH | 4.5 | 4.5 | 4.5 | 4.5 | 4.5 | 4.5 |
| Dispersibility | Poor | Poor | Medium | Medium | Medium | Good |

|  | Example 8g | Example 8h | Example 8i | Example 8j | Example 8k | Comparative Example 8a |
|---|---|---|---|---|---|---|
| Modified peptide (I) | 1 | 1 | 1 | 1 | 1 | 1 |
| Sodium polyoxyethylene(4.5) lauryl ether acetate | — | — | — | — | — | — |
| Sodium tetradecene sulfonate | 0.5 | 1 | 2 | 3 | 5 | — |
| Sodium polyoxyethylene(2) lauryl ether sulfate | — | — | — | — | — | — |
| Sodium N-coconut oil fatty acid acyl-L-glutamate | — | — | — | — | — | — |
| pH | 4.5 | 4.5 | 4.5 | 4.5 | 4.5 | 4.5 |
| Dispersibility | Poor | Medium | Medium | Good | Good | Poor |

Amount of Incorporation: Mass Ratio

In Examples 8c to 8f in which 3 parts by mass or more of sodium polyoxyethylene(4.5) lauryl ether acetate was incorporated relative to 1 part by mass of the modified peptide (I), it was confirmed that dispersibility of the modified peptide (I) increased. Furthermore, in Examples 8h to 8k in which 1 part by mass or more of sodium tetradecene sulfonate was incorporated relative to 1 part by mass of the modified peptide (I), it was confirmed that dispersibility of the modified peptide (I) increased.

The results for an evaluation of dispersibility of the modified peptide (I) in the hair treatment agents prepared as indicated in the following Table 9, the hair treatment agents having sodium polyoxyethylene(2) lauryl ether sulfate or sodium N-coconut fatty acid acyl-L-glutamate incorporated therein as an anionic surfactant, are presented below.

TABLE 9

| | Example 9a | Example 9b | Example 9c | Example 9d | Example 9e | Example 9f | Example 9g | Example 9h | Example 9i | Example 9j | Comparative Example 9a |
|---|---|---|---|---|---|---|---|---|---|---|---|
| Modified peptide (I) | 1 | 1 | 1 | 1 | 1 | 1 | 1 | 1 | 1 | 1 | 1 |
| Sodium polyoxyethylene(4.5) lauryl ether acetate | — | — | — | — | — | — | — | — | — | — | — |
| Sodium tetradecene sulfonate | — | — | — | — | — | — | — | — | — | — | — |
| Sodium polyoxyethylene(2) lauryl ether sulfate | 0.5 | 1 | 2 | 3 | 5 | — | — | — | — | — | — |
| Sodium N-coconut oil fatty acid acyl-L-glutamate | — | — | — | — | — | 2 | 3 | 4 | 5 | 10 | — |
| pH | 4.5 | 4.5 | 4.5 | 4.5 | 4.5 | 4.5 | 4.5 | 4.5 | 4.5 | 4.5 | 4.5 |
| Dispersibility | Poor | Poor | Medium | Medium | Good | Poor | Poor | Poor | Medium | Medium | Poor |

Amount of Incorporation: Mass Ratio

In Examples 9c to 9e in which 2 parts by mass or more of sodium polyoxyethylene(2) lauryl ether sulfate was incorporated relative to 1 part by mass of the modified peptide (I), it was confirmed that dispersibility of the modified peptide (I) increased. Furthermore, in Examples 9i and 9j in which 5 parts by mass or more of sodium N-coconut oil fatty acid acyl-L-glutamate was incorporated into 1 part by mass of the modified peptide (I), it was confirmed that dispersibility of the modified peptide (I) increased.

(Dispersibility of Modified Peptide (I) Liquid and Hydrolyzed Keratin Solution)

Dispersibility based on the difference in the pH of the modified peptide (I) liquid and a hydrolyzed keratin solution was evaluated. As an object of comparison for the modified peptide (I), a hydrolyzed keratin solution was prepared using hydrolyzed keratin of a commercially available product, by adding water to adjust the concentration of the hydrolyzed keratin to 1% by mass. Here, PROMOIS KR-30 manufactured by Seiwa Kasei Co., Ltd. was used as the hydrolyzed keratin of a commercially available product. The pH was adjusted to a predetermined value using citric acid and 2-amino-2-methyl-1-propanol.

The same evaluation method and evaluation criteria for dispersibility as those used for Tables 4 to 9 described above were employed.

The results for an evaluation of dispersibility in the samples prepared as indicated in the following Table 10, in which the pH of the modified peptide (I) liquid or the hydrolyzed keratin solution was adjusted, are presented below.

From the results of Table 10, in the modified peptide (I) liquid, when the pH was adjusted to 3.0 to 5.0, clouding or precipitation of the modified peptide (I) was observed. Furthermore, at pH 2.5 and pH 5.5, the modified peptide (I) was uniformly dispersed in the liquid, but cloudiness was observed. In the hydrolyzed keratin solution as an object of comparison, when the pH was adjusted to 2.0 to 4.5, clouding or precipitation of hydrolyzed keratin was observed. At pH 4.7, hydrolyzed keratin was uniformly dispersed in the liquid, but cloudiness was observed. Therefore, it could be confirmed that the modified peptide (I) liquid and the hydrolyzed keratin solution exhibited different dispersibility according to a difference in the pH. Thus, it is understood that the two liquids cannot be treated equally.

What is claimed is:

1. A hair treatment agent,
the hair treatment agent comprising:
(A) a modified peptide including side chain groups of Formula (I), the molecular weight of the modified peptide being 70,000 or less; and $$-S-S-(CH_2)_n-COOH \quad (I)$$

wherein in Formula (I), n represents 1 or 2;
(B) an anionic surfactant selected from alkyl ether carboxylic acid salts and present in an amount ranging from 9 parts by mass to 10 parts by mass, relative to 1 part by mass of the modified peptide; and
wherein the hair treatment agent has a pH of from 3.5 to 5.0.

2. The hair treatment agent according to claim 1, wherein the hair treatment agent is free of clouding and free of precipitation.

TABLE 10

| | pH | | | | | | | | | | | |
|---|---|---|---|---|---|---|---|---|---|---|---|---|
| | 7 | 6.5 | 6 | 5.5 | 5 | 4.7 | 4.5 | 4 | 3.5 | 3 | 2.5 | 2 |
| Modified peptide (I) liquid | Good | Good | Good | Medium | Poor | Poor | Poor | Poor | Poor | Poor | Medium | Good |
| Hydrolyzed keratin solution | Good | Good | Good | Good | Good | Medium | Poor | Poor | Poor | Poor | Poor | Poor |

3. The hair treatment agent according to claim 1, wherein the hair treatment agent is a liquid formulation.

4. The hair treatment agent according to claim 1, wherein the viscosity of the hair treatment agent is 1,000 mPa·s or less, wherein
the viscosity is a value obtainable by initiating measurement using a B-type viscometer and using an appropriate rotor at a speed of rotor rotation of 12 rpm at 25° C., and taking the measurement data 60 seconds after the initiation of measurement.

5. A method for treating hair, comprising:
applying the hair treatment agent according to claim 1 on the hair to penetrate the hair treatment agent into the hair and
washing the hair treatment away from the hair.

6. A method for treating hair, comprising:
applying the hair treatment agent according to claim 1 on the hair to penetrate the hair treatment agent into the hair and
finishing the treating hair without washing the hair treatment agent away from the hair.

7. A hair treatment agent,
the hair treatment agent comprising:
(A) a modified peptide including side chain groups of Formula (I), the molecular weight of the modified peptide being 70,000 or less; and $$-S-S-(CH_2)_n-COOH \qquad (I)$$

wherein in Formula (I), n represents 1 or 2;

(B) an anionic surfactant selected from alkyl ether carboxylic acid salts, α-olefin sulfonates, and alkyl ether sulfates, and present in an amount ranging from 7% to 15% by mass of the hair treatment agent; and wherein the hair treatment agent has a pH of from 4.5 to 5.5.

* * * * *